United States Patent
Nykaza

[11] Patent Number: 5,827,059
[45] Date of Patent: Oct. 27, 1998

[54] EZ WIPE DENTAL MIRROR

[76] Inventor: Robert Steven Nykaza, 130 Huntington Pl., Colorado Springs, Colo. 80906

[21] Appl. No.: 944,770

[22] Filed: Oct. 7, 1997

[51] Int. Cl.[6] ........................................................ A61B 1/24
[52] U.S. Cl. ................................................................ 433/30
[58] Field of Search ......................... 433/30, 31; 600/248

[56] References Cited

U.S. PATENT DOCUMENTS

| | | | |
|---|---|---|---|
| 2,608,708 | 9/1952 | Williamson | 433/30 X |
| 2,948,912 | 8/1960 | Wisdom | 433/30 X |
| 2,973,541 | 3/1961 | Beck | 433/30 X |
| 3,158,935 | 12/1964 | Rosenthal | 32/69 |
| 3,300,859 | 1/1967 | Sanden | 32/69 |
| 3,539,247 | 11/1970 | Broussard | 350/308 |
| 3,566,474 | 3/1971 | Zuhlke et al. | 32/69 |

*Primary Examiner*—Nicholas D. Lucchesi
*Attorney, Agent, or Firm*—Patent & Trademark Services; Thomas Zack; Joseph H. McGlynn

[57] ABSTRACT

A hand held dental mirror having a mirrored surface dental head and an extending handle wherein a wiper assembly is moved to slide over the mirrored surface by an external thumb member in the handle. The wiper assembly has a wiper arm on which is mounted a removable mirrored surface engaging wiper blade. Springs in the head maintain the replaceable wiper blade in a lowered position until a user moves the handle's exposed thumb member to overcome the action of the biasing springs and move the wiper to clean its mirrored head surface.

5 Claims, 1 Drawing Sheet

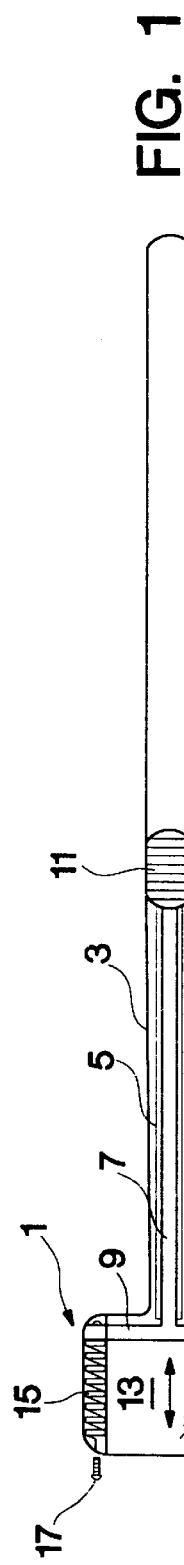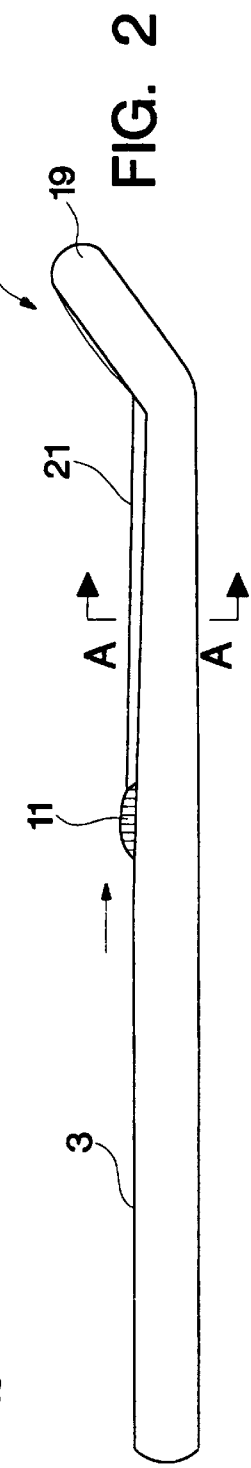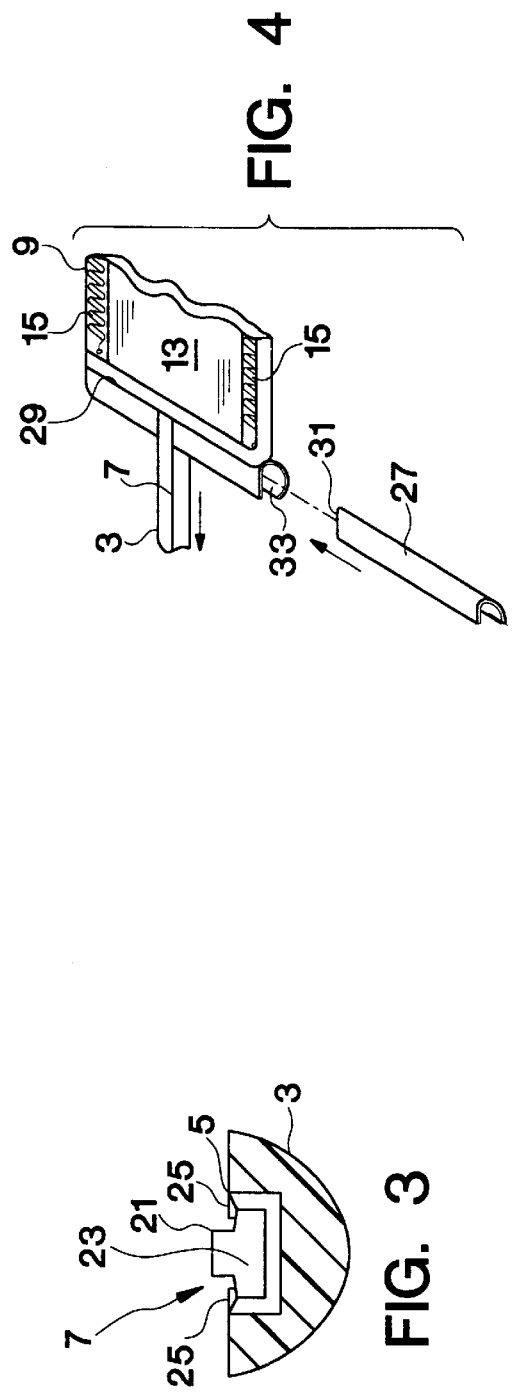

EZ WIPE DENTAL MIRROR

BACKGROUND OF THE INVENTION

Hand held mirrors used by dental personnel to visually observe different parts of a patience's oral cavity are known. When so used water spray and debris from dental procedures often causes the mirror's reflective surface to become obscure or otherwise not visually clear to the user. To remove the offending material the user usually removes the mirror from the patient's oral cavity and wipes it clean. For many professionals this is not only time consuming but requires a reorientation of the inserted cleaned mirror to the original field of vision. The present invention seeks to solve these problems by providing for a dental mirror which can be wiped clean while in the patient's oral cavity without changing its desired placed orientation as described herein.

DESCRIPTION OF THE PRIOR ART

Dental mirrors of different shapes and orientations have been around for many years. For example, in U.S. Pat. No. 3,158,935 to Rosenthal a dental mirror is disclosed having a wiper for its mirrored surface and a spring and rod in the handle that is actuated by an external thumb disc.

In the Sanden invention (U.S. Pat. No. 3,300,859), the dental mirror described has arcuate indentations at the upper and lower margins to allow for a more comfortable separation between the upper and lower teeth when inserted into an oral cavity.

The Broussard dental mirror (U.S. Pat. No. 3,539,247) has a movable film which can renew the reflecting qualities. A cleaning and wetting agent in the mirror's head housing immerses the film prior to moving it into place on the reflecting surface.

In U.S. Pat. No. 3,566,474 to Zuhlke et al. the disclosed dental mirror has a blank of light-reflecting material clamped between male and female frames portions which seeks to reduce the tarnish effect of interacting respiration air. The present invention provides for a dental mirror having a movable mirror wiper with biasing means in the mirror's head whose wiper is controlled by a thumb slide in the handle all as more further set forth in this specification.

SUMMARY OF THE INVENTION

This invention relates to a dental mirror having a mirrored surface dental head and an extending hand-held handle wherein a mirror surface wiper is actuated by a slide member in the handle. Biasing means in the dental head maintain the replaceable wiper in a lowered position until overcome by the action of the slide member.

It is the primary object of the present invention to provide for an improved dental mirror and wiper apparatus.

Another object is to provide for such an apparatus wherein biasing means keep the mirror's wiper out of the way until actuated by a slidable handle member.

These and other objects and advantages of the present invention will become apparent to readers from a consideration of the ensuing description and the accompanying drawings.

BRIEF DESCRIPTION OF THE DRAWINGS

FIG. 1 is a top view of the invention's preferred embodiment with the side covering portions of the dental head removed to shown its internal biasing springs.

FIG. 2 is a side view of the FIG. 1 embodiment.

FIG. 3 is a cross sectional enlarged view along lines A—A of the FIG. 2 handle as viewed towards the head.

FIG. 4 is an enlarged side perspective view of the front section showing the wiper assembly and the assembly's wiper blade being inserted on the wiper arm over the head's mirrored reflecting surface.

DESCRIPTION OF THE PREFERRED EMBODIMENT

FIG. 1 is a top view of the invention's preferred embodiment with the two opposite side covering portions of the dental head removed to shown its internal side biasing springs. The dental instrument generally consists of the square or rectangular (i.e., four interior right angled joined sides) head 1 with four rounded exterior side edges and the attached elongated extending handle portion 3. An elongated indented cut out handle track 5 extends partially along the length of the handle 3 to form a hollow cavity within the handle's front part to where it joins with the attached head. Mounted partially within the track 5 is a reciprocable rigid rod 7 whose front end is connected to the wiper assembly 9 with its head mounted wiper arm and a removable wiper blade. A manually operated exposed protruding thumb slide 11 movable with and forming a connected part of the rod 7 is used to reciprocate the attached wiper assembly 9 in the direction of the arrow across the face of mirrored surface 13. Two small side mounted biasing springs 15 held within side head cavities on opposite sides of the mirror 13 are engaged at their forward most ends by the spring retaining screws 17. Two side top covering (not shown in this cut away view) normally cover the tops of springs 15 to assist in retaining them within their respective mounted head side cavities.

FIG. 2 is a side view of the FIG. 1 embodiment showing one 19 of the two side coverings for the springs mounted in the head. These covering may be formed either integrally with the housing forming the head 1 or may be added thereto. The external portion 21 of rod 7 is visible in this view while the wider internal portion 23 of the rod is placed within the handle's cut out track. Movement of the exposed thumb slide 11 attached to rod 7 in the direction of the arrow forces two side contacting edges of the wiper assembly 9 against the normal biasing action of the side springs 15 to move the assembly and its attached mirror engaging wiper blade over the lower mirrored surface 13.

FIG. 3 is a cross sectional enlarged view along lines A—A of the FIG. 2 handle 3 as viewed in the direction of the head 1. The handle's interior cut out longitudinal track 5 receives the movable rod 7. This rod has an external exposed portion 21 and a wider interior track portion 23. Inwardly facing side handle lips 25 on both side of the rod along its length retain the rod portion 23 and hence the rod within the handle's track.

FIG. 4 is an enlarged side detailed perspective view of the wiper assembly 9 showing its removable wiper blade 27 being inserted on the reciprocable wiper arm 29 while positioned over the lower mirrored surface 13. The blade 27 has a U-shaped concave longitudinal cross section 31 which fits tightly over the complementary shaped longitudinal arm cross section 33 when inserted thereon from the side as shown by the arrow. By inserting the removable blade 27 on the wiper arm 29 the blade bears against the lower mirrored reflecting surface 13. To remove the blade from its wiper arm mount, the blade is simply moved in the opposite direction of the arrow by first slightly lifting the arm and blade out of engagement with the surface 13 and then sliding the blade. The two side biasing springs 15 move backward (to the left in this figure) when the wiper arm is lifted slightly out of engagement with them but may be compressed slightly at their engaged ends to bias the blade assembly after a new or cleaned blade 27 has been installed. This slight spring compression in the installation process is performed by bearing against the wiper's end and forcing the assembly to the right against the springs' ends. Other ways to attach the wiper blade to wiper arm are also possible such as by using a clip-on blade mounted which can be mounted on the raised wiper arm between the arm and the lower mirrored surface.

The mirror head 1, head springs and screws, the wiper assembly 9 with its blade and arm must all be of sufficiently small size to conventionally fit with the oral cavity of a patient. By making the wiper assembly manually operable by the thumb actuated exposed slide trigger 11, rather than electrically operable, the cost for the unit is maintained low while the user can use a modified pen grasp technique as commonly taught in most dental schools to manipulate the handle and within a patient's oral cavity. Thus, no new use techniques need to be taught to master the inventions movements within an oral cavity only the reciprocating movement of the slide trigger when there is a need to clean the mirrored surface. By making the head square or rectangular with exposed rounded edges, as contrasted to a mostly circular or oval head shape, the reciprocating wiper blade movement can clear most of the exposed mirrored surface since this surface occupies most of the visible head area as shown in the FIG. 1 top view.

The instrument components should be constructed of material that can meet the standards established by the Occupational Safety and Health Administration (OSHA) standards for cleaning and sterilization. This typically involves an ultrasonic cleaner or a chemical autoclave unit in order to clean and sanitize the unit's components being using them again.

Although the present invention's preferred embodiment and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A dental instrument having a mirrored surface comprising:

a dental instrument having a head with an exposed mirrored reflecting surface thereon and an attached extending hand-held handle;

a wiper assembly mounted on said reflecting surface and having an extending attached handle member fixed thereto with an internal slidable member, said wiper assembly being actuated by sliding the handle's slidable member to move the wiper assembly over the head's mirrored surface; and wiper assembly biasing means mounted in the dental instrument's head to normally maintain the wiper assembly in a first position until such biasing means is overcome by the manual action of a user on the slidable member to move the assembly over the mirrored surface.

2. The instrument as claimed in claim 1, wherein said dental instrument's head is substantially shaped with four interior right angles and rounded outer corners around said exposed mirrored reflecting surface.

3. The instrument as claimed in claim 1, wherein said handle member has an internal longitudinal cavity to mount its internal slidable member, said slidable member having an external protrusion extending from the internal handle cavity to manually move the slideable member within the cavity.

4. The instrument as claimed in claim 3, wherein said wiper assembly includes a wiper arm with a mounted removable wiper blade, said mounted blade being in contact with the mirrored reflecting surface to clean the surface when moved.

5. The instrument as claimed in claim 4, wherein said wiper assembly biasing means mounted in the dental instrument's head includes two springs mounted in head cavities on opposite sides of the mirrored reflecting surface in contact with the wiper assembly.

* * * * *